United States Patent
Ling et al.

[11] Patent Number: 6,019,766
[45] Date of Patent: Feb. 1, 2000

[54] ACETABULAR CUP CEMENT PRESSURIZATION DEVICE

[75] Inventors: Robin S. M. Ling, Dartmouth; Graham A. Gie, Yeoford; Andrew J. Timperley, St. Leonard's, all of United Kingdom; Donald W. Howie, Tennyson, Australia; Namal S. Nawana, Twickenham, United Kingdom; John A. Storer, Juaye Mondaye, France

[73] Assignee: Stryker Technologies Corporation, Kalamazoo, Mich.

[21] Appl. No.: 09/184,539

[22] Filed: Nov. 2, 1998

[30] Foreign Application Priority Data

Nov. 17, 1997 [GB] United Kingdom .................... 9724280

[51] Int. Cl.⁷ .................................................. A61B 17/58
[52] U.S. Cl. .............................................. 606/94; 606/86
[58] Field of Search ................................. 606/94, 92, 93, 606/95, 91, 86, 102; 623/22, 23

[56] References Cited

U.S. PATENT DOCUMENTS

| | | | |
|---|---|---|---|
| 4,324,006 | 4/1982 | Charnley | 623/22 |
| 4,327,449 | 5/1982 | Charnley | 623/22 |
| 5,501,687 | 3/1996 | Willert | 606/94 |
| 5,507,748 | 4/1996 | Sheehan | 606/94 |
| 5,527,317 | 6/1996 | Ashby et al. | 606/91 |
| 5,728,160 | 3/1998 | Draenert | 623/16 |

*Primary Examiner*—Michael Buiz
*Assistant Examiner*—Jonathan D. Goldberg
*Attorney, Agent, or Firm*—Lerner, David, Littenberg, Krumholz & Mentlik, LLP

[57] ABSTRACT

A device for use with an acetabular socket prosthesis which has an outer rim of predetermined size. The device comprises an outwardly extending removable location and/or sealing element adapted to surround the outer rim of said cup with which it is to be used during implantation thereof.

18 Claims, 4 Drawing Sheets

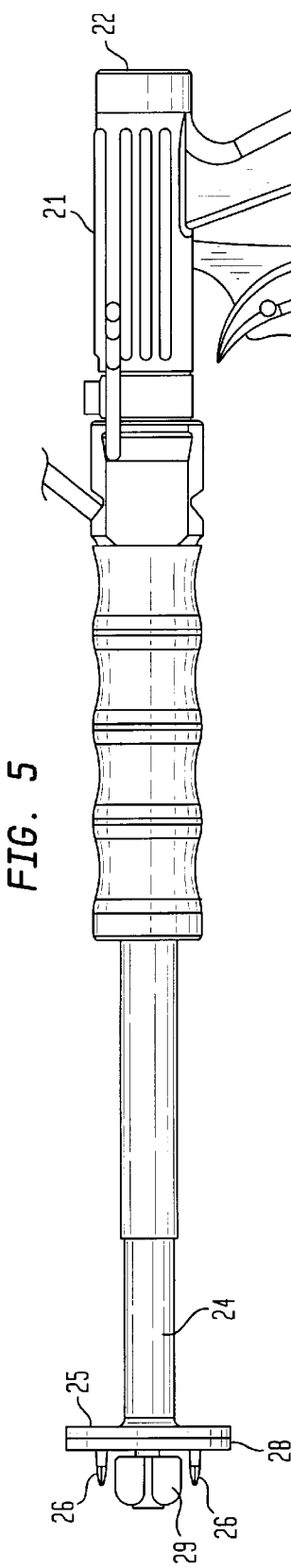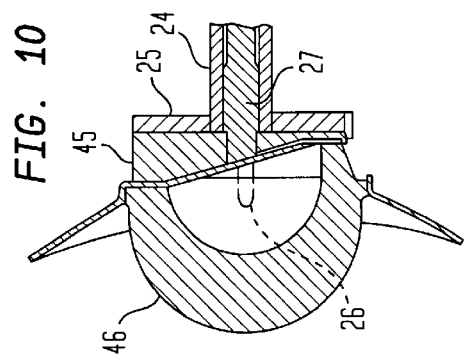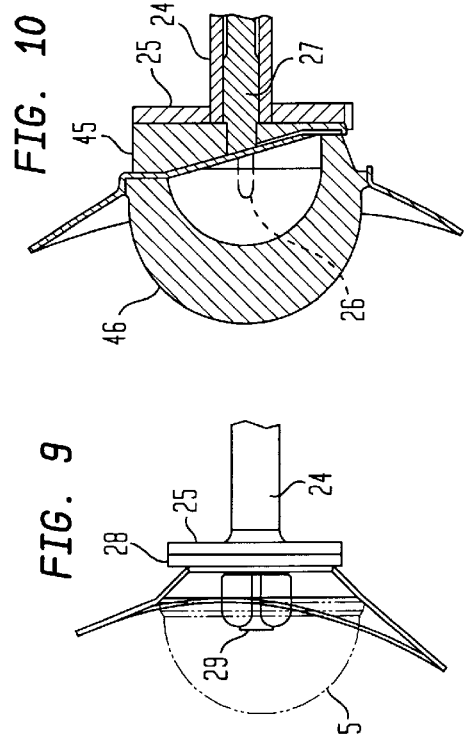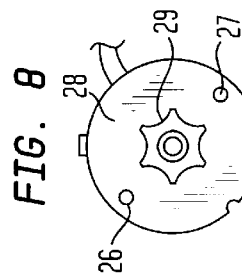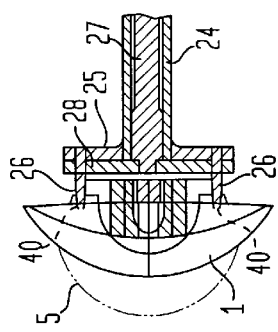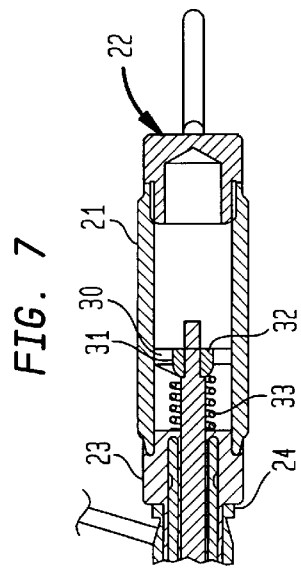

ACETABULAR CUP CEMENT PRESSURIZATION DEVICE

BACKGROUND OF THE INVENTION

1. Field of the Invention

This invention relates to a device to pressurize cement when implanting an acetabular cup and to the device, when provided with an acetabular cup, and to a combination of the device and cup with an inserter. The device is also useful for appropriately positioning acetabular cups or trial cups in a desired anatomical position.

2. Description of the Prior Art

In acetabular reconstruction, a replacement component in the form of an acetabular cup can be fixed to the patient by the use of bone cement. For cemented acetabular constructions commonly using polymethyl methacrylate as the cement, the pressurization of the cement at the time of surgery is critical to successful fixation. The time available to the surgeon to achieve the necessary pressurization once the cement has been introduced into the acetabulum and the positioning of the component is relatively short.

It is therefore important for the surgeon to be able to establish the exact position of the cup before it is introduced into the acetabulum of a patient which has been reamed out to receive it. The present invention is intended to provide a device which will improve the cement fixation and the alignment of the cup in the acetabulum. Cement sealing devices for acetabular cups are known in the prior art and are shown in U.S. Pat. Nos. 4,324,000, 4,327,449 (which both have flanges), 5,501,687 and 5,507,748. With known acetabular cups having outwardly extending flanges, there is a risk of abrading material from the face and edge of the flange, which may be plastic, thus causing abrasions when in contact with bone cement.

SUMMARY OF THE INVENTION

According to the present invention, a device for use with an acetabular socket prosthesis which has an outer rim of predetermined size comprises an outwardly extending removable location and/or sealing element adapted to surround the outer rim of the cup with which it is to be used during implantation thereof. This provides a device which will improve the cement fixation and alignment of the cup in the acetabulum.

Thus, the location element can be used to pressurize the cement surrounding the cup and can subsequently be removed, or the location element can be employed to locate the socket in the bone, or both. When the cup is pressurized into the socket, excess cement tends to squeeze out around the outer rim of the cup and the location element of the present invention enables this to be pressurized. When the cement is suitably set, the removable element can be taken away.

Preferably, the device is provided with structures for releasable attachment to an inserter tool for inserting the acetabular cup and the attachment structure can be constructed to allow the device to be attached between the cup and the tool.

With this arrangement the device can be arranged to be attached to the inserter tool so that it is removed with it or it can be arranged to be releasably connected to the cup itself and when the inserter tool has been removed and the cement reached a suitable setting, the removable element can be removed from the cup.

In a convenient construction, the element is in the form of a flange located on a central body portion and this can carry the structure for attachment to the inserter tool.

In one preferred construction the attachment element can act to retain the device on the inserter when the inserter is removed from the acetabular cup. With this arrangement therefore the cup is left in place and the device removed with the inserter.

According to another preferred embodiment, elements can be included for releasably securing the device to the acetabular cup and with this arrangement the attachment means can act to release the device from the inserter when the inserter is removed from the acetabular cup so that the device remains on the cup until the cement is suitably set and is then removed.

With this arrangement the device can be provided with an attachment portion which is a tight fit on the outer rim of the acetabular cup.

In another suitable embodiment the device can be provided with an attachment portion which is a snap fit onto the outer rim of the cup. In any case, the outwardly extending removable flange is preferably substantially part-spherical. With this arrangement the flange can be connected to the central body portion or to the portion that attaches to the cup at an angle between −45° and 60°.

Two edges of the flange defining the longest axis of the part-spherical fitting can be arranged at different angles. The device can be made from a material which is stiff enough to allow pressurization of the cement but sufficiently flexible to allow it to be trimmed. For example, the device can be made from high density polyethylene or nylon. Alternately, the device can be made of metal, glass, ceramic or other non-flexible material which can not be easily trimmed.

With this arrangement and even with flanges made of plastics material, the flange can be preformed and dimensioned for use without trimming. In this method of use the bone itself can be suitably trimmed to shape.

The body portion referred to above can act to seal the edge of the acetabular cup to prevent access of cement into the bearing surface thereof and if desired, a sealing member can also be included between the parts. The invention also includes a device as set forth above with an acetabular cup prosthesis.

Also provided within the scope of the invention is a device with an acetabular cup prosthesis as set forth above in combination with an inserter, said inserter having first and second relatively movable elements, means for securing said cup to said second element, said means extending past or through said first element, and means for moving said first and second elements apart to cause said securing means on said second element to detach from said cup.

With this arrangement, means can be included for securing the device to the second element so that the device is detached from the cup when said first and second elements are moved apart. The device can be used with a trial component to predetermine the size and position of the acetabular cup prior to cementing.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 5 is a side elevation of the inserter tool for use with the device shown in FIG. 1 according to the invention;

FIG. 6 is a cross-sectional plan view of the forward end of the inserter tool shown in FIG. 5;

FIG. 7 is a cross-sectional plan view of the rear end of the inserter tool shown in FIG. 5;

FIG. 8 is a front elevation of the inserter tool shown in FIG. 5;

FIG. 9 is a side elevation of the forward end of the inserter tool shown in FIG. 5 with the device in place;

FIG. 10 is a cross-sectional elevation of a modified form of the front end of the inserter tool shown in FIG. 5;

DESCRIPTION OF THE PREFERRED EMBODIMENT

Figure 1:
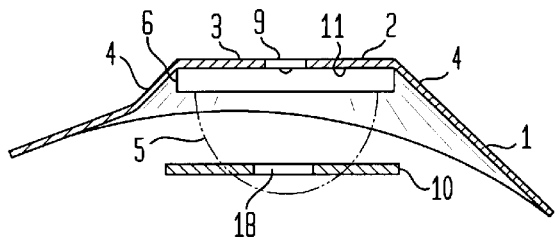
FIG. 1 is a cross-sectional side elevation of a device according to the invention.

A first embodiment of the device is shown in FIG. 1 and is intended for use with an acetabular cup prosthesis having an outer rim of predetermined size. The device comprises a location or sealing element which is provided by outwardly extending flange means which is located on a central body portion 2. The central body portion 2 has a generally flat surface 3 and a raised angular edge 4 to provide easy location of an acetabular cup indicated by broken lines 5 and having an outer rim 6 of predetermined size. The raised angular edge 4 can be omitted if desired and the outer flange means 1 can extend directly from the flat surface 3 of the body portion 2. Openings 7 and 8 are also provided in the central body portion 2 together with a central aperture 9 to enable the device to be connected to an introducer tool of the kind shown in FIG. 5.

A sealing element in the form of a sealing washer 10 can be provided (as shown in FIG. 1) for location between a lower flat surface 11 of the main body portion 2 and the cup 5 to be inserted. In FIG. 1 the washer is shown in a displaced position beneath the cup.

The flange means 1 has a part-spherical or conical configuration and is generally elliptical in plan view. The longest axis of the shape being indicated by center line 12 and the shorter axis by center line 13 in FIG. 2.

Figure 2:
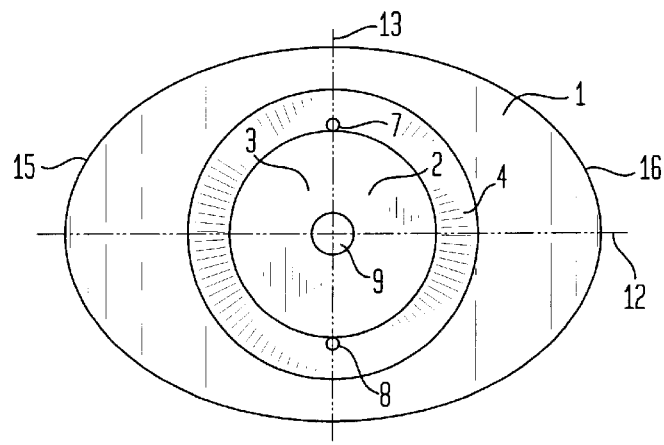
FIG. 2 is a plan view from above of the device shown in FIG. 1.
Figure 3:
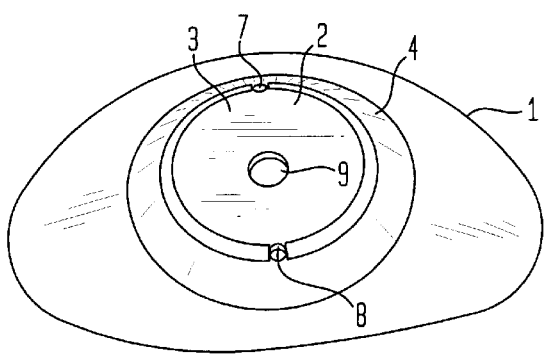
FIG. 3 is an isometric view from above of the device shown in FIG. 1.
Figure 4:
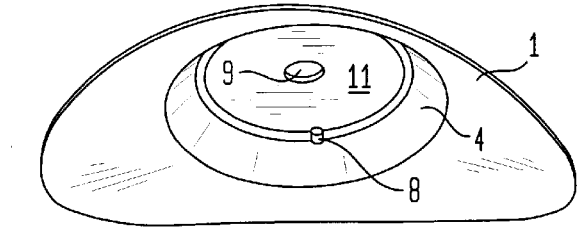
FIG. 4 is an isometric view from beneath of the device shown in FIG. 1.
Figure 11:
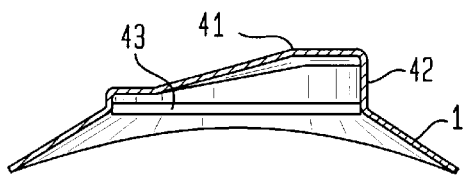
FIG. 11 is a cross-sectional side elevation of an alternative construction of the device according to the invention.
Figure 12:
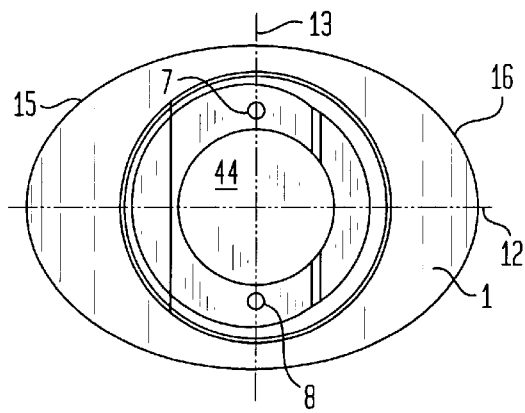
FIG. 12 is a plan view from above of the device shown in FIG. 11.
Figure 13:
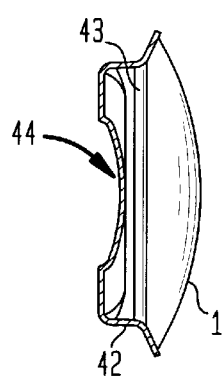
FIG. 13 is a cross-sectional end elevation of the device shown in FIGS. 11 and 12.
Figure 14:
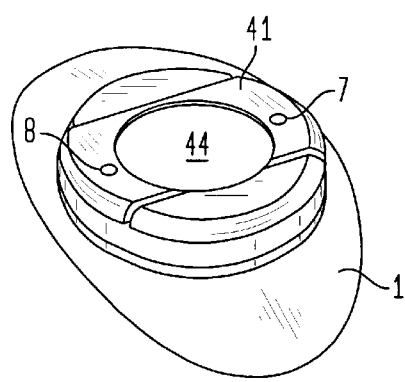
FIG. 14 is an isometric view from above of the device shown in FIG. 11.

As will be seen from FIG. 2, the openings 7 and 8 are partly in the center portion 2 and partly in the raised angular edge 4.

As will be seen from FIG. 1, the edges 15 and 16 on the longest axis 12 are raised at an angle which can be determined depending on the anatomical body portion on which it is to be used. This angle may range between −45° and 60° and is preferably between 0° and 45° with respect to the horizontal surface around the circumference of the device.

The central body portion 2 is made of a material that is stiff enough to allow pressurization of the cement but sufficiently flexible to allow the outer edges to be trimmed. It must also be sufficiently rigid to provide a solid connection with the introducer tool shown in FIG. 5 and to be described hereunder.

Although a plurality of polymeric materials can be used, it is preferred to use polyethylene, preferably high density polyethylene or nylon or some other suitable material.

The flange means 1 can be flexible in order to facilitate its trimming to the appropriate size for location on a patient's pelvis. However, the stiffness of the flange 1 must be sufficient to allow pressurization of cement introduced into the socket within which the cup is to be introduced. Again, while various types of polymer material can be used, nylon or high density polyethylene (HDPE) is preferred.

The flange can also be provided with a plurality of markings (not shown) showing diameter measurements and/or appropriate orientation of the device and these may be molded, machined or embossed on the flange 1.

The sealing element 10 shown in FIG. 1 is used to prevent access of cement around the outer rim 6 of the cup 5 and into the bearing surface (not shown). This sealing element can be in the form of a flexible ring and although it is preferred it may not be essential if sufficient sealing is provided by the lower surface 11 of the main body portion 2. The center of the sealing element 10 is provided with an opening 18 to allow it to be connected to the inserter in a manner to be described.

An introducer tool for use in the invention is shown in FIG. 5 and comprises a handle 20 to which is connected a handle mounting barrel 21, one end of which is closed by a screw threaded cap 22. The other end of the mounting barrel 21 is closed by a stop member 23 which carries a mounting tube 24. The displaced end of the tube 24 carries a second element in the form of a disc 25. The disc is provided with two attachment pins 26. Located within the mounting tube 24 is an operating rod 27, the outer end of which carries a first element provided by a disc 28 which has openings to allow the pins 26 to pass through it. The operating rod 27 is rigidly attached to the disc 28, but its outer end passes through an opening in the disc and is screw threaded to receive a locating nut 29. The other end of the operating rod 24 projects into the mounting barrel 21 and is engaged by an operating claw 30 which bears against a shoulder 31 on the rod. Between the shoulder and the claw 30 there is a collar 32, one side of which bears against a compression spring 33, the other end engaging the end of the stop 23. The claw 30 is provided on a trigger 34 carried on an extension 35 of the handle 20.

The arrangement is such that when the trigger 34 is pulled rearwardly, the claw 30 acts against the compression spring 33 to compress it and the rod 27 is moved longitudinally in the mounting tube 24, thus causing the discs 25 and 28, which constitute the first and second elements, to move apart. This movement effectively moves the disc 28 along the engagement pins 26 and 27.

The device to pressurize the cement is attached to the insertion tool by pushing the openings 7 and 8 over the pins 26 and so that the end of the rod 27 passes through the aperture 9. The nut 29 is now tightened down to hold the device against the outer disc 28. An acetabular cup can now be placed over the remainder of the pins 26, the cup being suitably provided with engagement holes 40 as indicated in FIG. 6 where the cup is shown in chain lines. Alternatively, a trial cup of similar configuration and having suitable openings can be used. Thus, the acetabular cup or trial cup is backed by the pressure device which is located between the cup and the introducer tool as shown in FIGS. 6 and 9. A sealing element 10 can be used if desired.

When the present invention is to be used, the patient's acetabulum is first reamed out and once the appropriate dimensions of the device have been obtained, a trial acetabular cup having a size and shape nearly identical to that of the final acetabular component is secured to the introducer tool in the manner shown in FIGS. 5 to 9. The trial cup is then introduced into the patient's acetabulum to verify its position.

When it has been established that the position of the trial cup is appropriate and the flange has been trimmed appropriately, the trial cup is then replaced by the cup which is to be implanted.

Cement is introduced into the acetabulum as required and the cup is then placed in position on the introducer and pressure is applied. The flange 1 allows the surgeon to maintain an appropriate pressure on the cement until it is nearly cured. The introducer release mechanism is now operated by pulling the trigger 34 which causes the discs 25 and 28 to move apart, thus removing the pins 26 from the cup. The introducer can now be safely removed at the same time, taking away the pressure device and leaving the cup in place.

FIGS. 11, 12, 13 and 14 show another construction of pressure device according to the invention. In this arrangement the same reference numerals are used to indicate similar parts as in FIGS. 1 to 4. In this construction, however, the main body is of a different shape to that shown in the earlier construction. In this arrangement the main body has a shaped upper surface 41 which is adapted to receive a prosthetic cup with an angled entrance. Such a cup is shown in position on the inserter in FIG. 10. The angled shape of the main portion is necessary to accommodate this shape. The main body portion extends downwardly to provide a cylindrical wall 42, the lower end of which immediately adjacent the flange portion 1 is shaped to be a tight fit onto the rim of the cup with which it is to be used. This engagement portion is indicated by reference numeral 43. The term "tight" is used herein to mean that the device, when pushed onto the rim of the cup, will not release unless pressure is applied in the opposite direction. As the materials are plastics materials, the tight fit might even be an "interference" fit if it is necessary, that is the diameter of the portion 43 might be the same as or even slightly less than the diameter of the outer rim of the cup. It will be appreciated that the whole intention is that the device should be held securely on the cup while it is being used, but can subsequently be removed. In an alternative construction, the arrangements could be such that the device is a "snap" fit onto the cup, the cup being dimensioned appropriately to receive it.

In this construction the opening 9 is replaced by a much larger opening 44.

The device shown in FIGS. 11 to 14 can be used with the same inserter as shown in FIG. 5, but in this case the nut 29 is removed and the first element, that is the disc 28, is also removed and replaced by a modified disc 45 as shown in FIG. 10. In this figure the cup is indicated by reference numeral 46.

In order to carry out the operation, the device is fastened onto the cup or a trial cup in the manner shown in FIG. 10 and placed on the pins 26. The operation is now carried out as described with regard to the construction shown in FIG. 1, but when the cement has cured the trigger 34 is operated, which pulls the pins 26 out of the cup and through the device so that the inserter can be removed. The device and its flange 1 remain on the cup and can be subsequently removed as desired by the surgeon.

Figure 15:
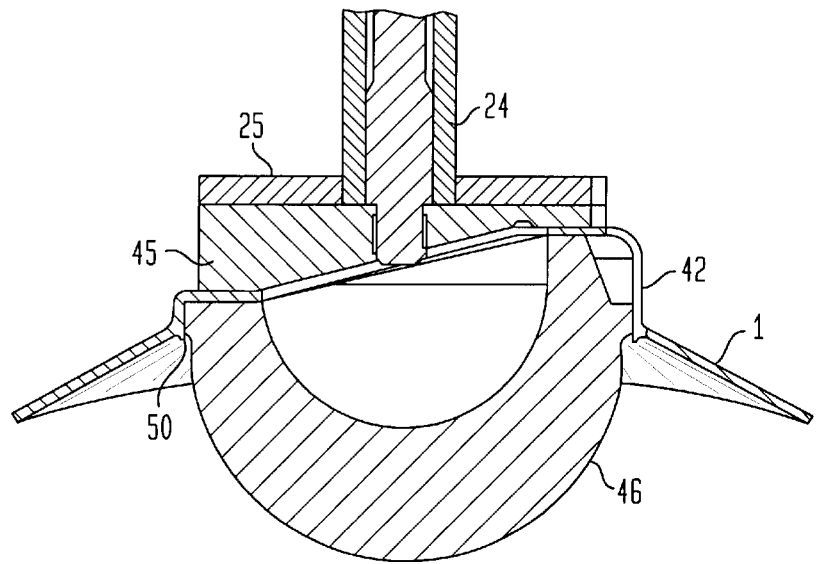
FIG. 15 is a cross-sectional side elevation of a modification of the construction shown in FIGS. 11 to 14.

FIG. 15 shows a modified construction of the device shown in FIGS. 11 to 14. The same reference numerals are used to described similar parts to those shown in FIGS. 10 to 14 but in this construction, a feather edge seal 15 is included around the rim of the cylindrical wall 42. This feature can be utilized to improve the sealing of the cup without the flange being a snap fit on the cup as is shown in FIGS. 11 to 14. This seal 50 comprises a short feather edged protrusion which can close slightly onto the cup to effect a seal when the cement is pressurized.

Figure 16:
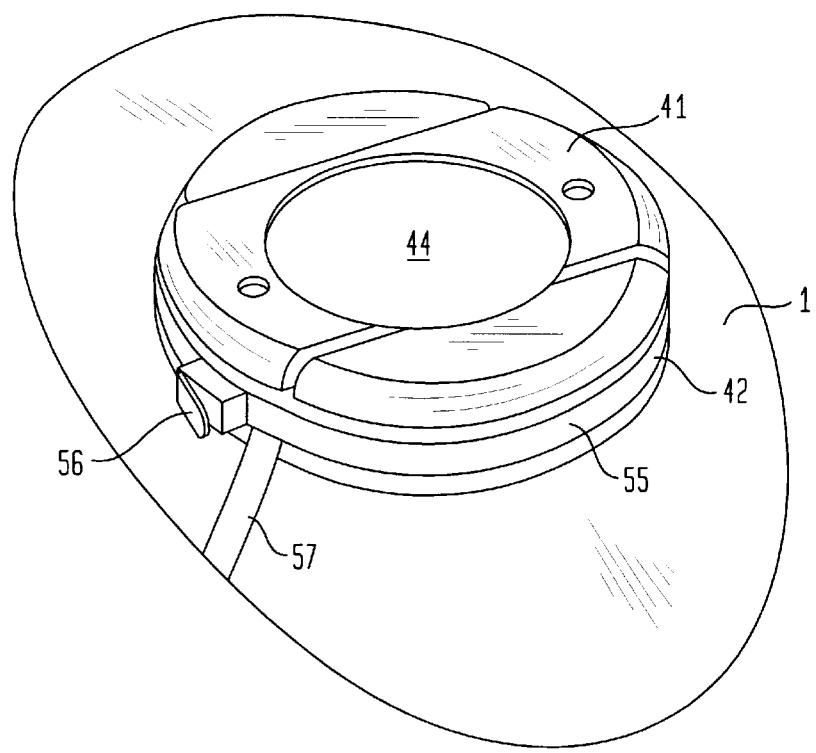
FIG. 16 is an isometric view from above of another form of construction of the device shown in FIGS. 11 to 15.

FIG. 16 shows another feature which can be incorporated into any of the devices described above. The particular device on which this feature is shown is similar to that illustrated in FIGS. 14 to 15. In this arrangement a feature is included to facilitate the removal of the flange when the cement has cured and comprises a "tear off" strip 55 bounded by lines of weakness and on operating flap 56 to start the tear. In the embodiment shown, the tear off strip is provided in the wall 42 but it could be provided at any convenient position to provide an annular line of weakness. The strip also extends along a substantially radial extension 57 to enable the outer annulus of the flange to be separated.

Although a tear off strip is shown, any other form of line of weakness which would assist in separating the various pars of the device and breading the annulus of the flange could be incorporated, the tear off strip merely being shown as a typical example.

In the construction described above, the flange is made of a synthetic plastics material but, if desired, it could be made of metal, glass, ceramic or other material which is not easily trimmed. In this method of using the device, the bone itself can be suitably trimmed to shape.

Again, in the construction described above, the overall shape of the flange is substantially part-spherical or conical, but it could be any desired overall shape and extend in any direction, for example, substantially flat, wavy, or with a varying angle or shape around its circumference and it could be forward or rearward facing.

If required, the shape of the flange could be made to suit an individual patient, for example by making a mold from a fitting or sizing. With this method of operation, it may not be necessary to trim either the flange or the bone. The sizing or fitting can be determined, for example, by use of a scan.

It will be understood that the thickness of the flange is not critical provided it acts as a suitable abutment onto the bone.

While several examples of the present invention have been described, it is obvious that many changes and modifications may be made thereunto, without departing from the spirit and scope of the invention.

We claim:

1. A device for use with an acetabular cup prosthesis which has an outer rim of predetermined size, comprising a central body portion and an outwardly extending removable sealing flange adapted to surround the outer rim of said cup with which it is to be used during implantation thereof with bone cement, a means for releasably attaching the device to an inserter tool used to insert the cup, said means for releasably attaching said device to said inserter tool is constructed to allow said device to be attached between said cup and the tool, said sealing flange is located on said central body portion and said outwardly extending removable flange is substantially part spherical.

2. The device as claimed in claim 1, in which said central body portion carries the means for attachment to the insertion tool.

3. The device as claimed in claim 2 in which said attachment means can act to retain said device on said inserter when the inserter is removed from said acetabular cup.

4. The device as claimed in claim 2 including means for releasably securing said device to said acetabular cup.

5. The device as claimed in claim 4 in which said attachment means can act to release said device from said inserter when the inserter is removed from said acetabular cup.

6. The device as claimed in claim 5 which is provided with an attachment portion which is a tight fit on the outer rim of said acetabular cup.

7. The device as claimed in claim 5 which is provided with an attachment portion which is a snap fit onto the outer rim of said acetabular cup.

8. The device as claimed in claim 1 which is made from a material which is stiff enough to allow pressurization of the cement but sufficiently flexible to allow it to be trimmed.

9. The device as claimed in claim 8 which is made from high density polyethylene or nylon.

10. The device as claimed in claim 1 which is made of metal, glass, ceramic or other material which is not easily trimmed.

11. The device as claimed in claim 1 in which said body portion acts to seal the edge of said acetabular cup to prevent access of cement into the bearing surface thereof.

12. The device as claimed in claim 11 provided with a sealing member to act between the body portion and the edge of the acetabular cup.

13. An introducer for introducing a prosthetic acetabular cup into an opening in the acetabulum comprising:

a first plate having a surface with a guide element extending outwardly therefrom;

a second plate mounted on said guide element and moveable outwardly away from said surface of said plate along said guide element;

a polymeric sealing flange mounted on said second plate for movement therewith, said polymeric sealing flange is substantially part spherical having a receiving portion for receiving the acetabular cup and a sealing portion for sealing the opening in the acetabulum; and a tubular mounting shaft having said first plate mounted thereon and having an actuator within said shaft operatively connected to said second plate for selectively moving said second plate and said polymeric sealing flange along said guide element with respect to said first plate.

14. The introducer as claimed in claim 13 in which said outwardly extending removable flange is connected to said central body portion or to the portion which attaches to the cup at an angle between −45° and 60°.

15. The introducer as claimed in claim 13 in which two edges of said flange defining the longest axis of a part-spherical fitting are raised at different angles.

16. The introducer as claimed in claim 13 which is made from material which is stiff enough to allow pressurization of the cement but sufficiently flexible to allow it to be trimmed.

17. The introducer as claimed in claim 13 which is made from high density polyethylene or nylon.

18. A device for use with an acetabular cup prosthesis which has an outer rim of predetermined size, comprising a central body portion and an outwardly extending removable sealing flange adapted to surround the outer rim of said cup with which it is to be used during implantation thereof with bone cement, a means for releasably attaching the device to an inserter tool used to insert the cup, said means for releasably attaching said device to said inserter tool is constructed to allow said device to be attached between said cup and the tool, said sealing flange is located on said central body portion and said outwardly extending removable flange is substantially part spherical with said outwardly extending removable flange being connected to said central body portion or to the portion which attaches to the cup at an angle between −45° and 60° and wherein two edges of said flange defining the longest axis of a part-spherical fitting are raised at different angles.

* * * * *